United States Patent [19]

Chesky et al.

[11] 4,029,101

[45] June 14, 1977

[54] ABSORBENT ARTICLE

[75] Inventors: Sheldon R. Chesky, Algonquin; Donald Patience, Barrington, both of Ill.

[73] Assignee: Colgate-Palmolive Company, New York, N.Y.

[22] Filed: Nov. 13, 1975

[21] Appl. No.: 631,768

Related U.S. Application Data

[62] Division of Ser. No. 503,887, Sept. 6, 1974, Pat. No. 3,954,107.

[52] U.S. Cl. .......................................... 128/290 R
[51] Int. Cl.² ........................................ A61F 13/16
[58] Field of Search ............... 128/284, 285, 290 R, 128/290 W, 290 P, 287

[56] References Cited

UNITED STATES PATENTS

| 3,570,492 | 3/1971 | Bettencourt | 128/290 R |
| 3,612,054 | 10/1971 | Matsuda et al. | 128/287 |
| 3,667,468 | 6/1972 | Nystrand et al. | 128/290 R |
| 3,699,966 | 10/1972 | Chapuis | 128/290 R |

*Primary Examiner*—Louis G. Mancene
*Assistant Examiner*—Robert F. Cutting
*Attorney, Agent, or Firm*—Powell L. Sprunger

[57] ABSTRACT

An absorbent article for the perineum comprising, an elongated absorbent pad assembly having a front surface for facing the perineum, a back surface, and separable side portions adjacent the front surface of the pad assembly. The side portions define a longitudinally extending channel adjacent the lateral mid-point of the pad assembly, such that the side portions separate during use to expose an increased area of the pad assembly.

9 Claims, 8 Drawing Figures

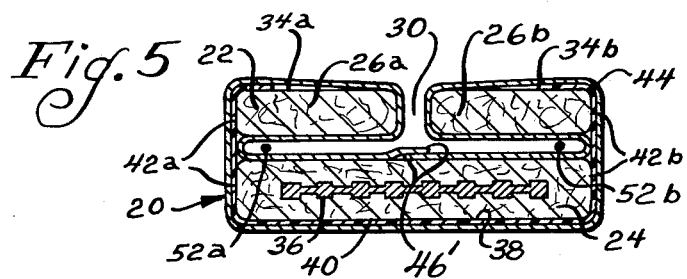
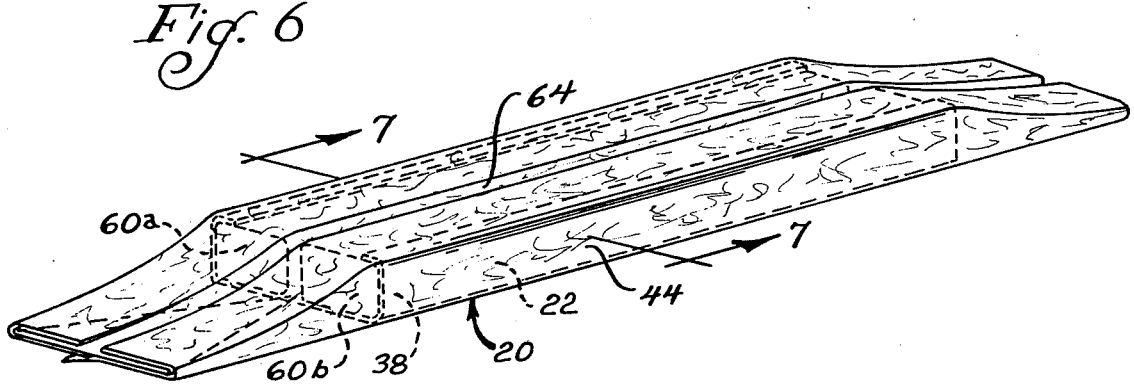
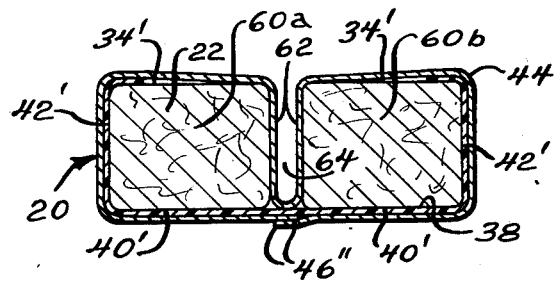
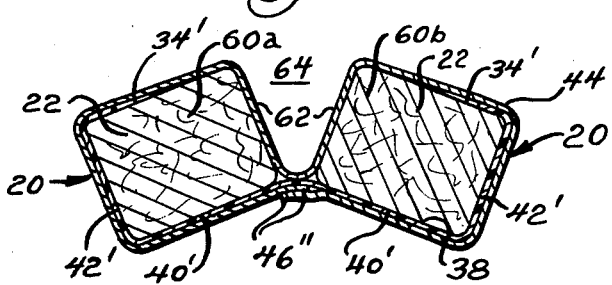

ABSORBENT ARTICLE

This is a division of application Ser. No. 503,887 filed Sept. 6, 1974, now U.S. Pat. No. 3,954,107, issued May 4, 1976.

BACKGROUND OF THE INVENTION

The present invention relates to absorbent articles, and more particularly to absorbent pads for the perineum.

A various assortment of absorbent pads having been proposed for use in the perineum to receive body exudates, such as sanitary and maternity pads to receive menses and lochia, and surgical or wound dressings. When properly positioned, such pads should normally form both a longitudinal and arcuate configuration due to the contour of the wearer's body in the perineum. Accordingly, it has been relatively difficult to obtain a proper fit of such pads which would provide comfort to the wearer and prevent leakage at the edges of the pads, particularly when the discharge is at its greatest. Moreover, many of such pads present a surface against the wearer's skin in the region of the discharge which becomes moist, resulting in discomfort to the wearer.

SUMMARY OF THE INVENTION

A principle feature of the present invention is the provision of absorbent pad means of simplified construction for the perineum which prevents leakage during use.

The pad means of the present invention comprises an elongated absorbent pad assembly having a front surface for facing the perineum, a back surface, and separable side portions adjacent the front surface of the pad assembly.

A feature of the invention is that the side portions define a longitudinally extending channel or well adjacent the lateral mid-point of the pad assembly to receive and trap body exudates.

Another feature of the invention is that the side portions separate during use to expose an increased surface area of the pad assembly which is spaced from the wearer's skin for absorbing the trapped body exudates into the pad assembly thus minimizing leakage.

Yet another feature of the invention is that body fluids are rapidly absorbed into the increased fluid receiving surface area resulting in drier surfaces of the pad assembly.

Still another feature of the invention is that the pad assembly provides an improved fit for the wearer.

Thus, a feature of the invention is that the pad assembly provides greater comfort to the wearer.

Further features will become more fully apparent in the following description of the embodiments of this invention and from the appended claims.

DESCRIPTION OF THE DRAWINGS

In the drawings:

FIG. 5 is a sectional view of another embodiment of the pad means of the present invention;

FIG. 6 is a perspective view of another embodiment of the pad means of the present invention;

FIG. 7 is a sectional view taken substantially as indicated along the line 7—7 of FIG. 6; and FIG. 8 is a sectional view of the pad of FIG. 6 illustrating the configuration assumed by the pad means when worn.

DESCRIPTION OF THE PREFERRED EMBODIMENTS

Although the pad means of the present invention is particularly suitable for use as a sanitary or maternity pad, it will be apparent that it may be used for other purposes, as desired. For example, the pad means may be used as surgical or wound dressings in the perineum, such as rectal or vaginal dressings.

Figure 1:
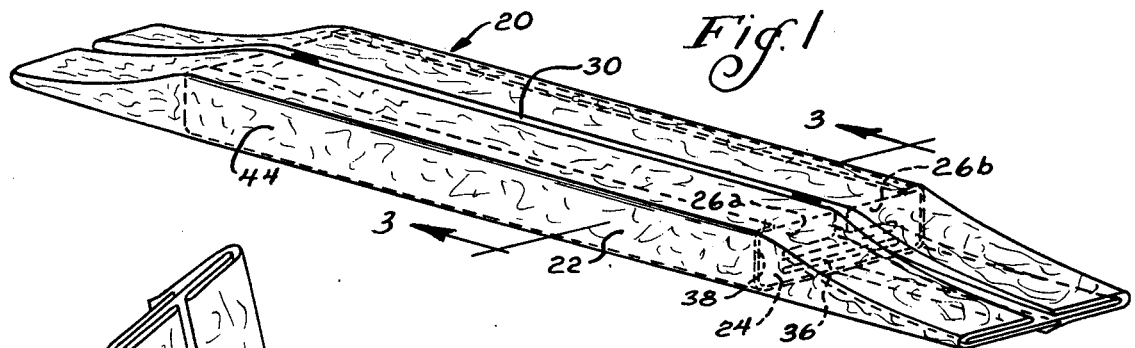
FIG. 1 is a perspective view of one embodiment of an absorbent pad means of the present invention.
Figure 2:
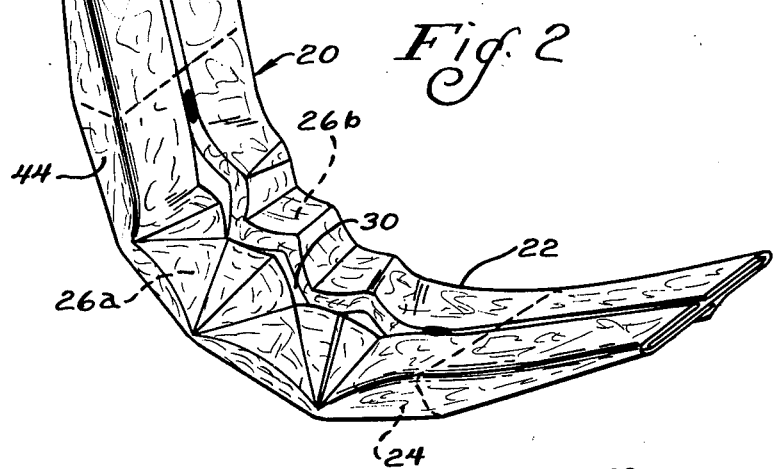
FIG. 2 is a perspective view illustrating the configuration assumed by the pad means of FIG. 1 when worn.
Figure 3:
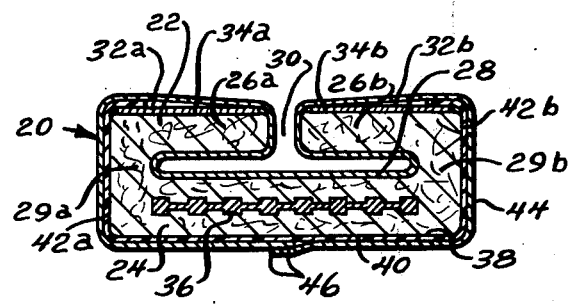
FIG. 3 is a sectional view taken substantially as indicated along the line 3—3 of FIG. 1.

Referring now to FIGS. 1-3, there is shown an absorbent pad means generally designated 20 having an elongated absorbent pad assembly 22. The pad assembly 22 has an elongated base pad 24, a pair of separated top pads 26a and 26b overlying a front surface 28 of the base pad 24, and a pair of elongated side sections 29a and b connecting the base pad 24 and top pads 26a and b. The pad assembly thus has a generally inverted T-shaped channel 30 intermediate the base pad 24, top pads 26a and b, and side sections 29a and b. The base and top pads may be made of any suitable material such as bleached wood fluff. A pair of elongated wadding sheets 32a and 32b, such as a cellulose material, may be positioned on the front surfaces 34a and 34b of the top pads 26a and b to provide structural integrity to the top pads. The base pad 24 may have an elongated baffle 36 extending through the base pad, as shown, to provide the base pad with additional absorption and wicking capacity, serving to spread liquid laterally through the pad assembly. The baffle may be made of any suitable material, such as embossed or plain absorbent cellulose wadding, or plastic. The pad assembly has a fluid resistant or impervious sheet 38, such as polyethylene, covering a back surface 40 of the base pad 24, outer side surfaces 42a and 42b of the base and top pads and connecting side sections, and a portion of the wadding sheets 32a and b adjacent the front surface of the top pads. The pad assembly 22 also has a fluid pervious top sheet 44, such as a nonwoven or gauze material, covering the exposed surfaces of the inverted T-shaped channel 30, the wadding sheets 32a and b, and the fluid impervious sheet 38. Marginal edges 46 of the top sheet 44 are overlapped and may be secured together adjacent the back surface 40 of the base pad 24.

As shown in FIG. 2, the pad means 20 forms both a lateral and longitudinal arcuate configuration when placed in the perineal area during use. Thus, when worn the top pads 26a and b of the pad assembly separate from each other causing the channel 30 to open. The opened channel 30 provides a pocket or well to receive body fluids, while exposing an increased surface area of the pad assembly. The body fluids are thus trapped in the well, and the increased exposed surface area of the pad assembly, which is spaced from the wearer's skin, rapidly absorbs and carries away the fluid into the pad assembly without impairment usually encountered when the fluid receiving surface is located adjacent the wearer's skin. The split pad assembly is particularly comformable to the body shape of the wearer in the perineum since the top pads are permitted to separate, and the fluid receiving surfaces of the pad assembly are spaced from the wearer's skin, as noted above, thus providing additional comfort to the wearer. The body fluids are channeled into the opened pad assembly for retention therein, and the pads, in conjunction with the fluid impervious sheet 38, prevent leakage during use.

Figure 4:
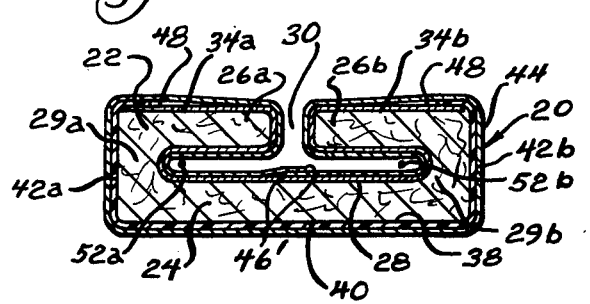
FIG. 4 is a sectional view of another embodiment of the pad means of the present invention.

Another embodiment of the pad means 20 is illustrated in FIG. 4, in which like reference numerals designate like parts. In this embodiment, a wadding sheet 48 covers the front surfaces 34a and b of the top panels 26a and b, and the exposed surfaces of the pad assembly facing the inverted T-shaped channel 30, as shown. The marginal edges 46' of the top sheet 44 may be overlapped adjacent the front surface 28 of the base pad 24. Moreover, portions of the top sheet 44 adjacent inner ends of the channel 30 may be secured together by suitable means 52a and 52b, such as adhesive, if desired. In this and other embodiments, the baffle 36 may be omitted from the base pad 24, if desired. In other respects, the pad means 20 of FIG. 4 is similar in structure and function to the pad means of FIGS. 1-3.

Another embodiment of the pad means 20 is illustrated in FIG. 5, in which like reference numerals designate like parts. In this embodiment, the pad assembly 22 has separate top pads 26a and b and a base pad 24. The top sheet 44 in the inverted T-shaped channel 30 extends adjacent to the fluid impervious sheet 38 at the outer side surfaces 42a and b of the pad assembly, as shown. Thus, the fluid impervious sheet 38 and top sheet 44 connect the top pads 26a and b to the base 24. The pad means 20 of FIG. 5 operates in a similar fashion to the pad means described in connection with FIGS. 1-4, with the top pads 26a and b separating during use to expose increased absorbent surface areas of the pad assembly.

Another embodiment of the pad means 20 is illustrated in FIGS. 6-8, in which like reference numerals designate like parts. As illustrated in FIGS. 6 and 7, the pad assembly 22 of this embodiment of a pair of elongated absorbent pads 60a and 60b disposed in a side-by-side relationship, with the pads 60a and b preferably having a generally rectangular cross-sectional shape. A fluid impervious sheet 38 covers the back surfaces 40', outer side surfaces 42', and a portion of the front surfaces 34' of the pads 60a and b. Thus, the fluid impervious sheet 38 connects the pads 60a and b, and serves as a hinge adjacent their back surfaces 40' to permit separation of the pads during use. Thus, the pads 60a and b of the pad assembly 22 define a fluid receiving channel 64 intermediate inner side surfaces 62 of the pads. A top sheet 44 covers the inner side surfaces 62, the front surface 34' of the pads 60a and b, and the fluid impervious sheet 38. Marginal edges 46'' of the top sheet 44 may be overlapped and secured together adjacent the back surfaces 40' of the pads.

When body fluids strike the absorbent surface of conventional sanitary pads, excessive time is required for the fluids to work into the pads, particularly for sudden surges of the fluids. Such pads often leave a wet surface, and provide only a highly localized area for absorption without use of a major portion of the pad surface. Accordingly, the body fluids cannot always be absorbed by the surfaces of such pads, resulting in frequent leakage.

During use of the pad means of the present invention, the pad assembly forms a generally arcuate configuration laterally and longitudinal through the pad means, such that the pads 60a and b separate adjacent their upper surfaces 34', as shown in FIG. 8. Thus, the fluid receiving channel 62 is opened when the pad means is worn to receive body fluids, while exposing recessed surface areas of the pad assembly for absorption of the fluids. Body fluids rapidly penetrate into the pads 60a and b and to the fluid impervious sheet 38, where the fluids are spread along the sheet to additional portions of the pads for absorption therein. Accordingly, the pad means maintains a relatively dry surface during use, and disperses fluids through the pads, while preventing leakage. It is also apparent that the pad means 22 has a simplified structure, and may be easily manufactured with reduced cost to the consumer.

Thus, there has been described an absorbent pad means which conforms to the contour of the wearer in the perineum, and provides an increased amount of absorptive surface area which is recessed from the wearer's skin for rapid passing of body fluids into the pad means, the pad means having an openable channel to direct fluids to the absorptive surface area.

The foregoing detailed description is given for clearness of understanding only, and no unnecessary limitations should be understood therefrom, as modifications will be obvious to those skilled in the art.

We claim:

1. Absorbent pad means for the perineum comprising, an elongated absorbent base pad having a front surface, a back surface, and a pair of outer side surfaces connecting said front and back surfaces, a pair of elongated top pads disposed in a side-by-side relationship and overlying the front surface of the base pad, said top pads being separate from said base pad and having a front surface for facing the perineum, a back surface facing the front surface of the base pad, and inner and outer side surfaces connecting the front and back surfaces, a fluid impervious sheet covering the back and outer side surfaces of the base pad and the outer side surfaces of the top pad, and a fluid pervious outer top sheet covering the fluid impervious sheet, the front, inner side, and back surfaces of the top pads and the front surface of the base pad, said fluid impervious and top sheets connecting said top pads to the base pad adjacent said outer side surfaces and the respective portions of said top sheet covering the inner side surfaces of the top pads being free of attachment in a fluid receiving region of the pad to permit relative free movement of the top pads aways from each other in the fluid receiving region and enlargement of a fluid receiving channel between the top pads.

2. The pad means of claim 1 including as elongated baffle extending through said base pad.

3. Absorbent pad means for the perineum, comprising:
   a. an elongated absorbent pad comprising,
      1. a base pad having a back surface and a front surface,
      2. a pair of separable top pads having a front surface, a back surface, and inner ends, said top pads overlying the base pad with the back surface of the top pads facing the front surface of the base pad, and with said inner ends having side surfaces facing each other at the top of said absorbent pad, and
      3. a pair of side sections extending between and connecting said top pads and base pad at sides of said absorbent pad, with said top pads, side sections and base pad defining an inverted T-shaped channel to receive body exudate;
b. a sheet of fluid impervious material covering the back surface of the base pad; and
c. a fluid pervious outer top sheet covering the front surface of the top pads, the side surfaces of the top pad inner ends, the back surface of the top pads, inner surfaces of said side sections, and the front surface of the base pad, with respective portions of the top sheet covering the opposed inner ends of the top pads being free of attachment in a fluid receiving region of the absorbent pad to permit relative free movement of said inner ends away from each other and enlargement of the channel between the top pads during use.

4. The pad means of claim 3 including a pair of wadding sheets covering the front surfaces of said top pad.

5. The pad means of claim 3 including a wadding sheet covering the front surfaces of said top pads and the exposed surfaces of the pad defining said inverted T-shaped channel.

6. The pad means of claim 3 wherein said pad includes outer side surfaces and said fluid impervious sheet covers at least a portion of said outer side surfaces.

7. The pad means of claim 6 wherein said fluid impervious sheet covers a portion of the front surfaces of said top pads.

8. The pad of claim 3 including adhering means securing the top sheet together intermediate said top and base portions and adjacent the inner ends of said inverted T-shaped channel.

9. The pad means of claim 3 including an elongated baffle extending through said base pad.

* * * * *